United States Patent
Sakano et al.

(10) Patent No.: US 7,105,693 B2
(45) Date of Patent: Sep. 12, 2006

(54) PROCESS FOR PRODUCTION OF ALKOXYSILANE-BASED COMPOUND

(75) Inventors: Yasunori Sakano, Annaka (JP); Noriyuki Koike, Yoshii-machi (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/753,340

(22) Filed: Jan. 9, 2004

(65) Prior Publication Data
US 2004/0143129 A1 Jul. 22, 2004

(30) Foreign Application Priority Data
Jan. 9, 2003 (JP) ............................. 2003-002792

(51) Int. Cl.
*C07F 11/00* (2006.01)
(52) U.S. Cl. ....................................... 556/60
(58) Field of Classification Search ................... 556/60
See application file for complete search history.

(56) References Cited

U.S. PATENT DOCUMENTS 5,493,044 A * 2/1996 Schwindeman ............. 556/471

FOREIGN PATENT DOCUMENTS

| JP | 06287305 | 10/1994 |
|----|----------|---------|
| JP | 2688469 | 12/1997 |
| WO | WO 9612723 | 5/1996 |

OTHER PUBLICATIONS

Yamatani Masaaki, "Preparation of (Meth) Acrylic-functional Organosilicon Compound," Patent Abstracts of Japan, Feb. 28, 1995, vol. 1995, No. 1.

* cited by examiner

*Primary Examiner*—Johann Richter
*Assistant Examiner*—Chukwuma Nwaonicha
(74) *Attorney, Agent, or Firm*—Millen, White, Zelano, Branigan, P.C.

(57) ABSTRACT

A process for producing an alkoxysilane-based compound having the general formula:

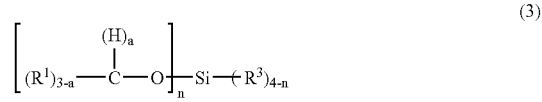

(3)

wherein, $R^1$ is an unsubstituted or substituted monovalent hydrocarbon group of 1 to 20 carbon atoms which may contain an ether linkage oxygen atom, or a group of a formula: $R^2O$— where $R^2$ is an unsubstituted or substituted monovalent hydrocarbon group of 1 to 20 carbon atoms which may contain an ether linkage oxygen atom, $R^3$ has an identical definition to that of $R^1$, a is 0 or 1, and n is 1, 2, or 3, wherein (a) an alcohol compound of the formula (1):

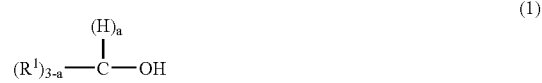

(1)

wherein, $R^1$ and a are as defined above, and (b) a halogenated organosilicon compound of the general formula (2):

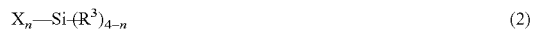

(2)

wherein, $R^3$ and n are as defined above, and X is a chlorine, bromine or iodine atom, are subjected to a dehydrohalogenation reaction in presence of (c1) a tertiary amine other than (c2) described below, and (c2) 1,8-diazabicyclo[5.4.0]undecene-7 and/or 1,5-diazabicyclo[4.3.0]nonene-5.

21 Claims, No Drawings

PROCESS FOR PRODUCTION OF ALKOXYSILANE-BASED COMPOUND

BACKGROUND OF THE INVENTION

1. Field of the Invention

The present invention relates to a process for producing an alkoxysilane-based compound in an industrially applicable manner, which uses a secondary alcohol or a tertiary alcohol as a raw material.

2. Description of the Prior Art

Conventionally, the most commonly known process for producing an alkoxysilane-based compound is a process in which, as shown below, an alcohol and a halogenated silicon compound are subjected to a dehydrohalogenation reaction in the presence of a tertiary amine.

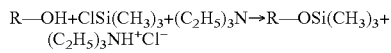

(wherein, R represents a monovalent hydrocarbon group)

In those cases in which a primary alcohol such as methyl alcohol is used as a reaction raw material, the reaction of the above process proceeds substantially quantitatively, enabling an efficient production of the target compound.

However, in the above process, if a secondary alcohol or a tertiary alcohol is used as the reaction raw material, then the reaction rate of the above reaction slows significantly compared to the case in which a primary alcohol is used. Particularly in cases where an attempt is made to react a dichlorosilane compound with a 2-fold mol equivalent of a secondary alcohol or a tertiary alcohol to form a disubstituted product, or in cases where an attempt is made to react a trichlorosilane compound with a 3-fold mol equivalent of a secondary alcohol or a tertiary alcohol to form a trisubstituted product, an extremely long reaction time is needed, the reaction yield is poor, and because the product also contains residual unreacted raw materials, as well as partially reacted components such as monosubstituted products, the target product must be isolated by distillation, which further reduces the yield of the target compound.

On the other hand, Japanese Patent publication No. 2,688,469 discloses a process for producing a (meth)acrylic functional group-containing organosilicon compound through a dehydrohalogenation reaction of (meth)acrylic acid and a haloalkyl group-containing organosilicon compound, wherein the reaction is conducted in the presence of 1,8-diazabicyclo[5.4.0]undecene-7 (hereafter referred to as "DBU"), which functions as a hydrogen halide acceptor.

However, DBU is expensive, and the use of large quantities of DBU as an industrial raw material is undesirable from a cost perspective, and in addition, a step for isolating and recovering the DBU is necessary, using filtration to separate the salt of DBU and the hydrogen halide produced in the reaction, and then washing the isolated salt with an aqueous alkali solution, and so even from a process perspective, the use of DBU is unfavorable.

SUMMARY OF THE INVENTION

An object of the present invention is to provide a process for producing an alkoxysilane-based compound efficiently, at a high reaction rate, and under favorable cost conditions, using a secondary alcohol or a tertiary alcohol as a raw material.

Taking the above problems into consideration, the inventors of the present invention investigated the use of DBU within the production of alkoxysilane-based compounds from a secondary alcohol or a tertiary alcohol and a halogenated organosilicon compound, based on the use of DBU in the process disclosed in the above reference publication, which is similar in so far as also being a dehydrohalogenation reaction. As a result, they discovered that by combining a comparatively small proportion of DBU with a conventionally used tertiary amine, the reaction rate could be improved dramatically, and the target compound could be produced efficiently and with a high yield, and as a result of further intensive investigation based on this discovery, they were able to complete the present invention.

In other words, the present invention provides, as a solution to the above object, a process for producing an alkoxysilane-based compound represented by a general formula (3) shown below:

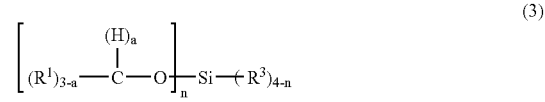

[wherein, each $R^1$ represents, independently, either an unsubstituted or substituted monovalent hydrocarbon group of 1 to 20 carbon atoms, which either contains, or does not contain, an ether linkage oxygen atom within a chain, or a group represented by a formula: $R^2O-$ (wherein, $R^2$ represents an unsubstituted or substituted monovalent hydrocarbon group of 1 to 20 carbon atoms, which either contains, or does not contain, an ether linkage oxygen atom within a chain), $R^3$ has an identical definition to that of $R^1$ above, a represents an integer of either 0 or 1, and n represents an integer of 1, 2, or 3], wherein (a) an alcohol compound represented by a general formula (1) shown below:

[wherein, $R^1$ and a are as defined above], and (b) a halogenated organosilicon compound represented by a general formula (2) shown below:

[wherein, $R^3$ and n are as defined above, and X represents a chlorine atom, a bromine atom, or an iodine atom] are subjected to a dehydrohalogenation reaction in presence of:

(c1) a tertiary amine other than (c2) described below, and (c2) 1,8-diazabicyclo[5.4.0]undecene-7 and/or 1,5-diazabicyclo[4.3.0]nonene-5.

DETAILED DESCRIPTION OF THE PREFERRED EMBODIMENTS

As follows is a more detailed description of the present invention.

[Raw Material Compounds]

—Component (a)—

The component (a), which represents a raw material compound for the process of the present invention is a secondary alcohol or a tertiary alcohol represented by a general formula (1) shown below:

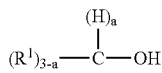 (1)

[wherein, each $R^1$ represents, independently, either an unsubstituted or substituted monovalent hydrocarbon group of 1 to 20 carbon atoms, and preferably from 5 to 15 carbon atoms (which may contain an ether linkage oxygen atom within the chain), or a group represented by a formula: $R^2O$— (wherein, $R^2$ represents an unsubstituted or substituted monovalent hydrocarbon group of 1 to 20 carbon atoms, and preferably from 5 to 15 carbon atoms (which may contain an ether linkage oxygen atom within the chain)), and a represents either 0 or 1].

Specific examples of the above $R^1$ groups include alkyl groups such as methyl groups, ethyl groups, n-propyl groups, isopropyl groups, n-butyl groups, tert-butyl groups, pentyl groups, and hexyl groups; cycloalkyl groups such as cyclopentyl groups and cyclohexyl groups; aryl groups such as phenyl groups; aralkyl groups such as benzyl groups and phenylethyl groups; alkenyl groups such as vinyl groups and allyl groups; alkynyl groups such as ethynyl groups; alkoxyalkyl groups such as methoxymethyl groups, methoxyethyl groups, ethoxyethyl groups, and (2-methoxy)ethoxymethyl groups; as well as groups in which either a portion of, or all of, the hydrogen atoms in the above groups have been substituted with halogen atoms such as chlorine atoms or fluorine atoms, including fluorinated alkyl groups such as trifluoromethyl groups, 3,3,3-trifluoropropyl groups, and groups represented by the formulas: $C_4F_9$—, $C_6F_{13}$—, $C_8F_{17}$—, $C_4F_9$—$CH_2CH_2$—, $C_6F_{13}$—$CH_2CH_2$—, and $C_8F_{17}$—$CH_2CH_2$—; and fluorinated alkoxyalkyl groups such as $CF_3O$—$C_2F_4O$—$CF_2$— and $C_3F_7O$—$C_3F_6O$—$CF(CF_3)$—.

Furthermore, in those cases in which $R^1$ is a group represented by the above formula $R^2O$—, specific examples of the group include alkoxy groups such as methoxy groups and ethoxy groups; alkenoxy groups such as vinyloxy groups and allyloxy groups; aryloxy groups such as phenoxy groups; alkoxyalkoxy group such as methoxymethoxy groups, methoxyethoxy groups, ethoxyethoxy groups, and (2-methoxy)ethoxymethoxy groups; as well as groups in which either a portion of, or all of, the hydrogen atoms in the above groups have been substituted with halogen atoms such as chlorine atoms or fluorine atoms, including fluorinated alkoxyalkoxy groups represented by the formulas: $CF_3O$—, $CF_3O$—$C_2F_4O$—, and $C_3F_7O$—$C_3F_6O$—.

Specific examples of the secondary alcohol or tertiary alcohol represented by the above general formula (1) are shown below, although the invention is not restricted to these compounds.

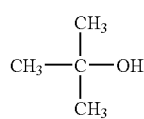 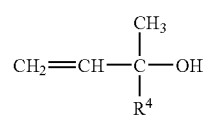

(wherein, $R^4$ represents a hydrogen atom or an alkyl group of 1 to 15 carbon atoms. This definition also applies in the following formulas.)

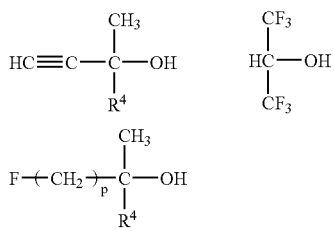

(wherein, p is an integer from 0 to 10)

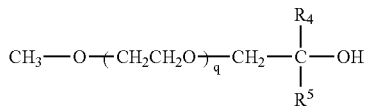

(wherein, $R^5$ represents a hydrogen atom or an alkyl group of 1 to 15 carbon atoms, and q is an integer from 0 to 9)

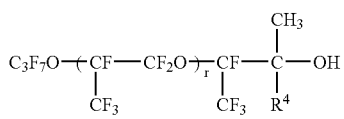

(wherein, r is an integer from 0 to 6)

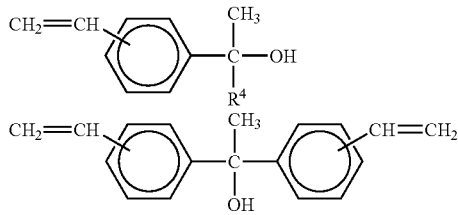

—Component (b)—

On the other hand, the component (b), which represents a raw material compound for the process of the present invention, is a halogenated organosilicon compound represented by a general formula (2) shown below:

 (2)

[wherein, $R^3$ has the same definition as $R^1$ in the general formula (1) above, X represents a chlorine atom, a bromine atom, or an iodine atom, and n represents 1, 2, or 3].

Specific examples of the halogenated organosilicon compound represented by the above general formula (2) are shown below, although the invention is not restricted to these compounds.

Cl—Si—$(CH_3)_3$, $Cl_2$—Si—$(CH_3)_2$, $Cl_3$—Si—$CH_3$, Cl—Si$(CH_3)_2(CH$=$CH_2)$, Cl—Si$(CH_3)(CH$=$CH_2)_2$, Cl—Si$(CH$=$CH_2)_3$, Br—Si$(CH_3)_2(CH$=$CH_2)$, Br—Si$(CH$=$CH_2)_3$

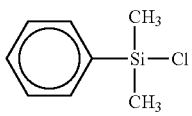

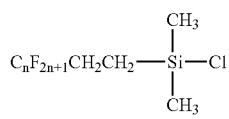

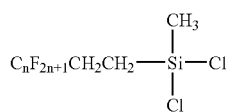

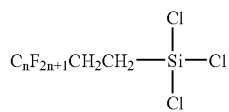

(wherein, in each of the above formulas, n is an integer from 1 to 10)

[Tertiary Amines]

The tertiary amines used in the process of the present invention perform the function of capturing the hydrogen halide generated by the reaction between the aforementioned component (a) and the component (b), forming a salt, and accelerating the reaction.

—Component (c1)—

The component (c1) used in the process of the present invention is a tertiary amine other than those of the component (c2) described below, and specific examples include trialkylamines in which alkyl groups of 1 to 6 carbon atoms are bonded to a nitrogen atom, such as triethylamine, tripropylamine, tributylamine, trimethylamine, diethylmethylamine, and butyldimethylamine. Aryl-based amines such as diethylphenylamine, and heterocyclic compounds such as pyridine can also be used.

These compounds of the component (c1) can be used singularly, or in combinations of two or more different compounds.

—Component (c2)—

The component (c2) used in the process of the present invention is either: 1,8-diazabicyclo[5.4.0]undecene-7 (DBU),

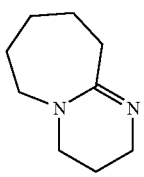

1,5-diazabicyclo[4.3.0]nonene-5.

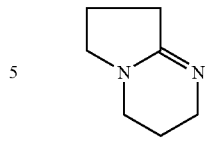

or a mixture of the two compounds,

[Reaction Conditions]

The quantities used of the alcohol of the component (a) and the halogenated organosilicon compound of the component (b) can be adjusted to any proportional combination, although using a quantity of the component (a) that is equivalent to 1.0 to 1.5 mols, and preferably from 1.0 to 1.2 mols, per 1 mol of halogen atoms within the component (b) is most effective in terms of reaction efficiency.

The use of the tertiary amines described above is a characteristic feature of the process of the present invention, and by combining a small proportion of the DBU or the like of the component (c2) with the tertiary amine of the component (c1), the reaction rate of the dehydrohalogenation reaction can be improved dramatically. In the present invention, the quantity used of the DBU or the like of the component (c2) is preferably comparatively small, and a quantity within a range from 0.3 to 20 mol %, and preferably from 0.5 to 10 mol %, relative to the combined quantity of the component (c1) and the component (c2) is sufficient.

If the quantity used of the component (c2) is too small, then the effect of the combination with the component (c1) in improving the reaction rate is limited, whereas in contrast, if the quantity is too large, no further improvement in reaction rate can be expected, and the process becomes undesirable from a cost perspective. The quantity of tertiary amine used as a base during the reaction [the combination of (c1) and (c2)] is preferably within a range from 1.0 to 1.5 mols per 1 mol of halogen atoms within the component (b).

A process for producing an alkoxysilane-based compound of the present invention is conducted in a reaction system containing the secondary alcohol or tertiary alcohol of the component (a), the halogenated organosilicon compound of the component (b), and the tertiary amines of the component (c1) and the component (c2), and there are no particular restrictions on the method used for introducing the raw materials. For example, the component (c1) and the component (c2) can be added to the secondary alcohol or tertiary alcohol of the component (a), either together or separately, and this mixture then subjected to stirring and mixing while the halogenated organosilicon compound of the component (b) is added dropwise.

As the reaction proceeds, because salts of the hydrogen halide and the tertiary amines are produced, making stirring gradually more difficult, a suitable quantity of solvent may be added if necessary to dilute the reaction mixture. In such a case, the solvent is preferably a hydrocarbon-based solvent with a boiling point of 40 to 180° C., and preferably from 70 to 120° C., and specific examples of suitable solvents include hexane, heptane, octane, benzene, toluene, xylene, and petroleum ether.

The reaction time for the process of the present invention varies depending on factors such as the quantity of raw materials, and cannot be specified, although the reaction of a conventional process that does not use the component (c2) and requires approximately 2 to 16 hours, can be completed in the much shorter time of 30 minutes to 1 hour using the process of the present invention. There are also no particular restrictions on the reaction temperature, although values from 0 to 100° C. are typical. Because the process of the present invention is an exothermic reaction, in order to increase the final reaction ratio, the system is preferably cooled to ensure the reaction temperature is maintained at no more than 60° C.

Following completion of the reaction, the target alkoxysilane-based compound can be obtained using an isolation operation that is suited to the properties of the target material, such as distillation.

EXAMPLES

As follows is a more detailed description of the present invention based on a series of examples, although the present invention is in no way restricted to the examples presented.

Example 1

A 1 liter 4-necked flask equipped with a condenser, a stirring device and a thermometer was flushed with nitrogen, and then 78 g (0.926 mols) of an alcohol represented by a formula (4) shown below,

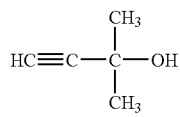

79 g (0.784 mols) of triethylamine, 3.58 g (0.0235 mols) of DBU and 78 g of toluene were placed in the flask, and the resulting mixture was stirred. Subsequently, 200 g (0.356 mols) of a dichlorosilane represented by a formula (5) shown below:

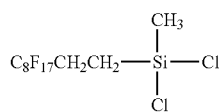

was added dropwise to the reaction system, under a nitrogen atmosphere, over a period of 30 minutes. During this addition, cooling was conducted to maintain the temperature of the reaction system at no more than 60° C.

Following completion of the dropwise addition of the dichlorosilane, stirring was continued for a further 30 minutes, and subsequent analysis of the composition of the reaction liquid using gas chromatography (GC) revealed a reaction ratio for the chlorine atoms of the dichlorosilane (that is, a production ratio for the disubstituted product) of 100%. Neither unreacted dichlorosilane nor monosubstituted products could be detected.

Subsequently, 200 g of water was added to the reaction system, and following stirring, the mixture was allowed to stand for 30 minutes in a separating funnel, and the bottom layer of the two separated layers, which was a toluene solution (the organic phase) containing the target product, was recovered.

The thus obtained toluene solution was washed with 200 g of water twice, and then distilled, yielding 190 g of an alkoxysilane (GC purity: 99.9%) represented by a formula (6) shown below, with a boiling point range from 116 to 118° C. at 0.27 KPa (2 mmHg).

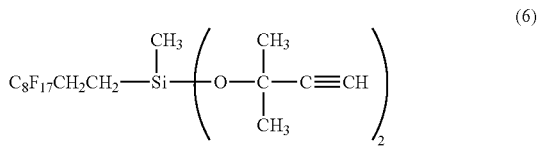

The isolated yield, calculated relative to the quantity added of the dichlorosilane represented by the above formula (5), was 81%.

Example 2

A 1 liter 4-necked flask equipped with a condenser, a stirring device and a thermometer was flushed with nitrogen, and then 84 g (0.994 mols) of the alcohol of the example 1 represented by the formula (4), 85 g (0.841 mols) of triethylamine, 1.27 g (0.00841 mols) of DBU and 84 g of toluene were placed in the flask, and the resulting mixture was stirred. Subsequently, 260 g (0.764 mols) of a monochlorosilane represented by a formula (7) shown below:

was added dropwise to the reaction system, under a nitrogen atmosphere, over a period of 30 minutes. During this addition, cooling was conducted to maintain the temperature of the reaction system at no more than 60° C.

Following completion of the dropwise addition of the monochlorosilane, stirring was continued for a further 30 minutes, and subsequent analysis of the composition of the reaction liquid using gas chromatography (GC) revealed a reaction ratio for the chlorine atom of the monochlorosilane of 100%, and unreacted monochlorosilane could not be detected.

Subsequently, 200 g of water was added to the reaction system, and following stirring, the mixture was allowed to stand for 30 minutes in a separating funnel, and the bottom layer of the two separated layers, which was a toluene solution (the organic phase) containing the target product, was recovered.

The thus obtained toluene solution was washed with 200 g of water twice, and then distilled, yielding 248 g of an alkoxysilane (GC purity: 100%) represented by a formula (8) shown below, with a boiling point range from 104 to 106° C. at 0.27 KPa (2 mmHg).

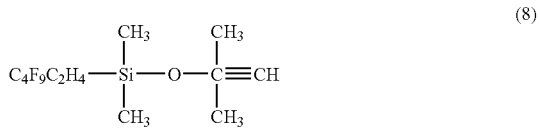

The isolated yield, calculated relative to the quantity added of the monochlorosilane represented by the above formula (7), was 84%.

Comparative Example 1

With the exceptions of altering the quantity of triethylamine to 81.6 g (0.806 mols), and not using the DBU, the same operations as the example 1 were conducted up until the completion of the dropwise addition of the dichlorosilane. Following completion of the dropwise addition of the dichlorosilane, stirring was continued for a further 15 hours, and subsequent analysis of the composition of the reaction liquid using gas chromatography (GC) revealed a reaction ratio for the chlorine atoms of the dichlorosilane of 42%.

Comparative Example 2

With the exceptions of replacing the DBU with 1.86 g (0.0235 mols) of pyridine, the same operations as the example 1 were conducted up until the completion of the dropwise addition of the dichlorosilane. Following completion of the dropwise addition of the dichlorosilane, stirring was continued for a further 15 hours, and subsequent analysis of the composition of the reaction liquid using gas chromatography (GC) revealed a reaction ratio for the chlorine atoms of the dichlorosilane of 46%.

Comparative Example 3

With the exceptions of altering the quantity of triethylamine to 93.5 g (0.0925 mols), and not using the DBU, the same operations as the example 2 were conducted up until the completion of the dropwise addition of the monochlorosilane. Following completion of the dropwise addition of the monochlorosilane, stirring was continued for a further 3 hours, and subsequent analysis of the composition of the reaction liquid using gas chromatography (GC) revealed a reaction ratio for the chlorine atom of the monochlorosilane of 36%.

Comparative Example 4

With the exceptions of only using 12.2 g (0.806 mols) of DBU, and not using the triethylamine, the same operations as the example 1 were conducted up until the completion of the dropwise addition of the dichlorosilane. Following completion of the dropwise addition of the dichlorosilane, stirring was continued for a further 1 hour, and subsequent analysis of the composition of the reaction liquid using gas chromatography (GC) revealed a reaction ratio for the chlorine atoms of the dichlorosilane (that is, a production ratio for the disubstituted product) of 100%, which was the same result as the example 1.

This result shows that by combining the DBU with triethylamine, the same effects can be achieved even if the quantity of the DBU is reduced.

According to the present invention, the reaction rate of a secondary alcohol or a tertiary alcohol with a halogenated organosilicon compound, and the yield of the alkoxysilane-based target compound can be improved, and in addition, problems of cost are minimal.

What is claimed is:

1. A process for producing a compound of the formula:

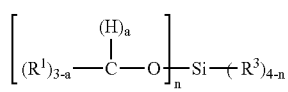  (3)

wherein each $R^1$ and each $R^3$ represents, independently, an optionally substituted monovalent hydrocarbon group of 1–20 carbon atoms, optionally containing an ether linkage oxygen atom within a chain, or a group represented by a formula: $R^2O$—, wherein $R^2$ represents an optionally substituted monovalent hydrocarbon group of 1–20 carbon atoms, optionally containing an ether linkage oxygen atom within a chain, a represents an integer of 0 or 1, and n represents an integer of 1, 2, or 3, comprising a dehalogenation reaction of:

(a) an alcohol of the formula (1):

  (1)

and (b) a compound of the formula (2):

$$X_n\text{—Si}\text{--}(R^3)_{4-n} \qquad (2)$$

wherein X represents a chlorine atom, a bromine atom, or an iodine atom, provided that at least one $R^1$ is alkynyl and/or at least one $R^3$ is a halogenated monovalent hydrocarbon, in the presence of:

(c1) a tertiary amine which is not a compound of (c2) described below, and (c2) 1,8-diazabicyclo[5.4.0]undecene-7 and/or 1,5-diazabicyclo[4.3.0]nonene-5.

2. A process according to claim 1, wherein the component (a) is a tertiary alcohol of the formula:

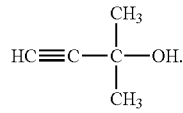

3. A process according to claim 1, wherein the component (b) is a compound of the formula:

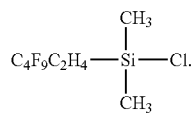

4. A process according to claim 1, wherein the component (b) is a compound of the formula:

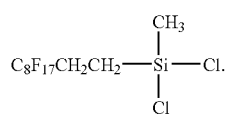

5. A process according to claim 1, wherein a quantity of the component (a) is within a range from 1.0–1.5 mols per 1 mol of halogen atoms within the component (b).

6. A process according to claim 1, wherein the component (c1) is at least one tertiary amine of a trialkylamine wherein alkyl groups of 1–6 carbon atoms are bonded to a nitrogen atom, diethylphenylamine, or pyridine.

7. A process according to claim 6, wherein the trialkylamine is at least one of triethylamine, tripropylamine, tributylamine, trimethylamine, diethylmethylamine, or butyldimethylamine.

8. A process according to claim 1, wherein a combined quantity of the component (c1) and the component (c2) is within a range from 1.0–1.5 mols per 1 mol of halogen atoms within the component (b).

9. A process according to claim 1, wherein the component (a) and the component (b) are subjected to a dehydrohalogenation reaction in the presence of the component (c1), the component (c2), and a hydrocarbon-based solvent with a boiling point of 40–180° C.

10. A process for producing a compound of the formula:

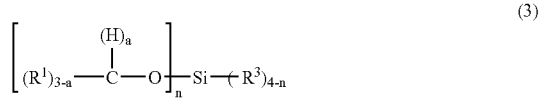

wherein each $R^1$ and each $R^3$ represents, independently, an optionally substituted monovalent hydrocarbon group of 1–20 carbon atoms, optionally containing an ether linkage oxygen atom within a chain, or a group represented by a formula: $R^2O-$, wherein $R^2$ represents an optionally substituted monovalent hydrocarbon group of 1–20 carbon atoms, optionally containing an ether linkage oxygen atom within a chain, a is 0, and n represents an integer of 1, 2, or 3, comprising a dehalogenation reaction of:

(a) a compound of the formula:

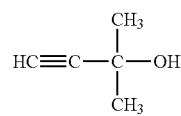

and, (b) a compound of the formula (2)

wherein X represents a chlorine atom, a bromine atom, or an iodine atom, in the presence of:
(c1) a tertiary amine other than (c2) described below, and
(c2) 1,8-diazabicyclo[5.4.0]undecene-7 and/or 1,5-diazabicyclo[4.3.0]nonene-5.

11. A process for producing a compound of the formula:

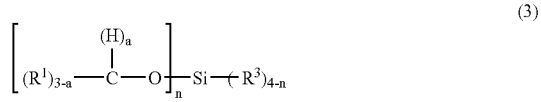

wherein each $R^1$ and each $R^3$ represents, independently, an optionally substituted monovalent hydrocarbon group of 1–20 carbon atoms, optionally containing an ether linkage oxygen atom within a chain, or a group represented by a formula: $R^2O-$, wherein $R^2$ represents an optionally substituted monovalent hydrocarbon group of 1–20 carbon atoms, optionally containing an ether linkage oxygen atom within a chain, a represents an integer of either 0 or 1, and n represents an integer of 1, 2, or 3, comprising a dehalogenation reaction of:

(a) a compound of the formula (1):

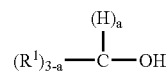

and (b) a compound of the formula (2)

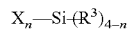

wherein X represents a chlorine atom, a bromine atom, or an iodine atom, in the presence of:
(c1) at least one tertiary amine of triethylamine, tripropylamine, tributylamine, trimethylamine, diethylmethylamine, or butyldimethylamine and (c2) 1,8-diazabicyclo[5.4.0]undecene-7 and/or 1,5-diazabicyclo[4.3.0]nonene-5.

12. A process according to claim 11, wherein the compound of the formula (1) is a tertiary alcohol.

13. A process according to claim 1, wherein $R^1$ and $R^3$ are each, independently, methyl, ethyl, n-propyl, isopropyl, n-butyl, tert-butyl, pentyl, hexyl, cyclopentyl, cyclohexyl, phenyl, benzyl, phenylethyl, vinyl, allyl, ethinyl, methoxymethyl, methoxyethyl, ethoxyethyl, (2-methoxy)ethoxymethyl, trifluoromethyl, 3,3,3-trifluoropropyl, $C_4F_9-$, $C_6F_{13}-$, $C_8F_{17}-$, $C_4F_9-CH_2CH_2-$, $C_6F_{13}-CH_2CH_2-$, $C_8F_{17}-CH_2CH_2-$, $CF_3O-C_2F_4O-CF_2-$, $C_3F_7O-C_3F_6O-CF(CF_3)-$, methoxy, ethoxy, vinyloxy, allyloxy, phenoxy, methoxymethoxy, methoxyethoxy, ethoxyethoxy, (2-methoxy)ethoxymethoxy, $CF_3O-$, $CF_3O-C_2F_4O-$ or $C_3F_7O-C_3F_6O-$.

14. A process according to claim 1, wherein the compound of formula (2) is: $Cl-Si-(CH_3)_3$, $Cl_2-Si-(CH_3)_2$, $Cl_3-Si-CH_3$, $Cl-Si(CH_3)_2(CH=CH_2)$, $Cl-Si(CH_3)(CH=CH_2)_2$, $Cl-Si(CH=CH_2)_3$, $Br-Si(CH_3)_2(CH=CH_2)$, $Br-Si(CH=CH_2)_3$,

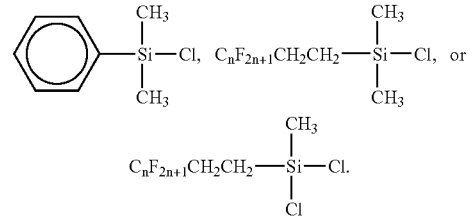

15. A process according to claim 9, wherein the solvent is hexane, heptane, octane, benzene, toluene, xylene or petroleum ether.

16. A process according to claim 10, wherein the tertiary amine is at least one of triethylamine, tripropylamine, tributylamine, trimethylamine, diethylmethylamine, or butyldimethylamine.

17. A process according to claim 3, wherein the tertiary amine is at least one of triethylamine, tripropylamine, tributylamine, trimethylamine, diethylmethylamine, or butyldimethylamine.

18. A process according to claim 4, wherein the tertiary amine is at least one of triethylamine, tripropylamine, tributylamine, trimethylamine, diethylmethylamine, or butyldimethylamine.

19. A process according to claim 1, wherein the component (a) and the component (b) are subjected to a dehydrohalogenation reaction in the presence of toluene.

20. The process according to claim 1, wherein the amount of the component (c2) based on the combined amount of the component (c1) and component (c2) together is within a range of 0.3–20 mol%.

21. The process according to claim 1, wherein a in formula (1) is 0.

* * * * *